United States Patent [19]

Kerch et al.

[11] Patent Number: 4,762,124

[45] Date of Patent: Aug. 9, 1988

[54] LIQUID DISPENSING POUCH

[75] Inventors: Martha E. Kerch, Sparta; Louis S. Hoffman, Morristown, both of N.J.

[73] Assignee: Kimberly-Clark Corporation, Neenah, Wis.

[21] Appl. No.: 924,098

[22] Filed: Oct. 28, 1986

[51] Int. Cl.⁴ ............................................. A61L 15/00
[52] U.S. Cl. ..................................................... 128/156
[58] Field of Search ................. 128/157, 155; 604/306

[56] References Cited

U.S. PATENT DOCUMENTS

| | | | |
|---|---|---|---|
| 2,035,357 | 3/1936 | Wright | 132/78.5 |
| 2,501,544 | 3/1950 | Shrontz | 128/156 |
| 2,579,403 | 12/1951 | Slomowitz et al. | 604/306 |
| 2,682,873 | 7/1954 | Evans et al. | 128/156 |
| 2,932,052 | 4/1960 | Morse | 15/209 |
| 2,992,644 | 7/1961 | Plantinga et al. | 128/156 |
| 3,334,374 | 8/1967 | Watkins | 15/539 |
| 3,334,790 | 8/1967 | Eaton | 222/107 |
| 3,366,112 | 1/1968 | Antonik | 128/157 X |
| 3,386,619 | 6/1968 | Douglas | 221/135 |
| 3,485,349 | 12/1969 | Chaney | 206/56 |
| 3,652,174 | 3/1972 | Boone | 401/143 |
| 3,657,760 | 4/1972 | Kudisch | 15/104.93 |
| 3,965,519 | 6/1976 | Hermann | 15/104.93 |
| 4,226,232 | 10/1980 | Spence | 128/156 |
| 4,519,798 | 5/1985 | Dinias | 128/156 X |

FOREIGN PATENT DOCUMENTS

| | | |
|---|---|---|
| 2430404 | 6/1974 | Fed. Rep. of Germany . |
| 2708931 | 3/1977 | Fed. Rep. of Germany . |
| 1031007 | 6/1953 | France . |

Primary Examiner—Gregory E. McNeill
Attorney, Agent, or Firm—William D. Herrick

[57] ABSTRACT

A liquid dispensing pouch in which a support, a liquid impregnated pad, permeable membrane and cover layer are peripherally joined in a layered arrangement by adhesive or heat seal means. The layers are coextensive and the impregnated pad is contoured to provide enhanced liquid-holding capabilities. The liquid is dispensed by peeling off the cover layer and bringing the membrane surface into contact with the skin.

9 Claims, 3 Drawing Sheets

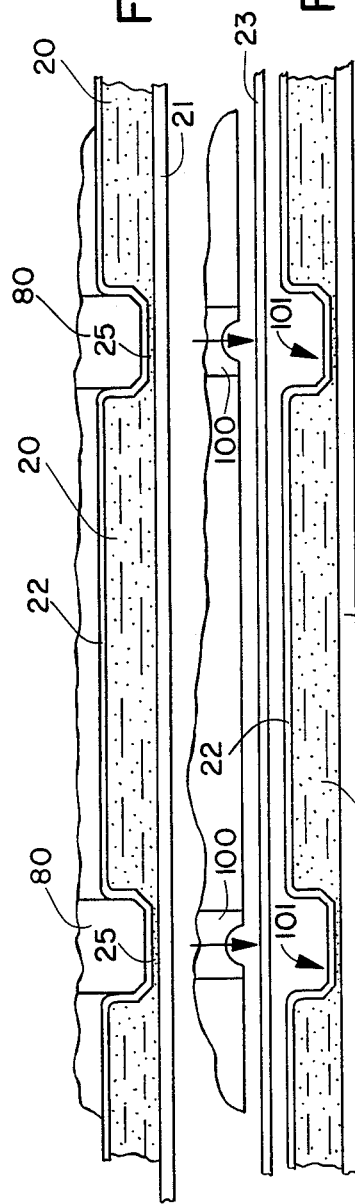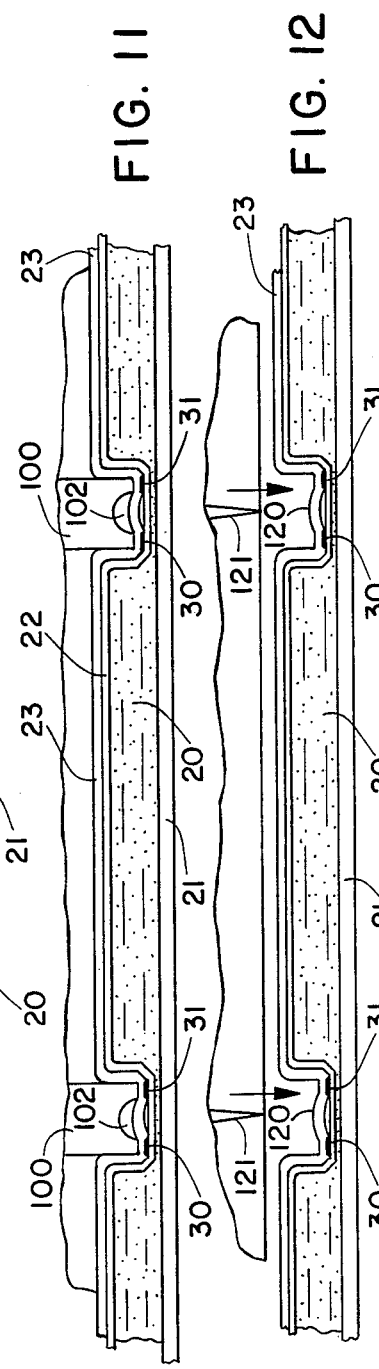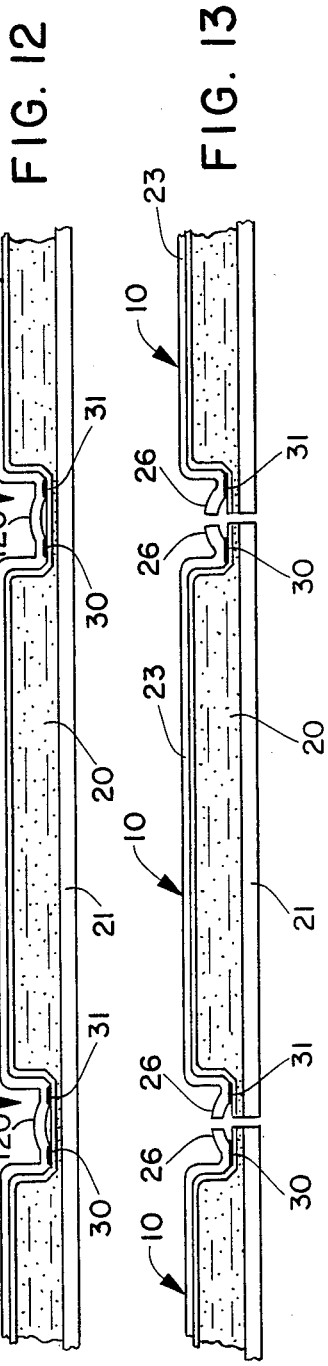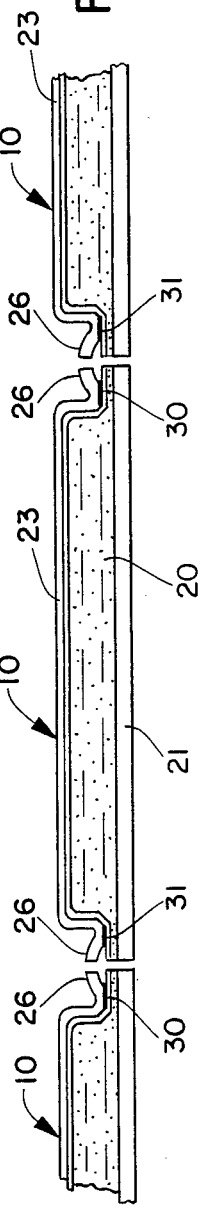

LIQUID DISPENSING POUCH

This invention relates to applicator pouches for dispensing liquids such as cosmetics and medicinal formulations and to a method for their manufacture.

These applicators are flexible composite packages comprised of several coextensive layers joined together by peripheral heat or adhesive seals. The liquid is contained within an absorbent pad which is uniquely structured to enhance its liquid-dispensing capabilities.

The liquid is dispensed by peeling off an impermeable cover and applying the liquid topically through a permeable membrane. A lubricating layer is continuously formed on the membrane surface so that the liquid may be applied to the skin with a very low coefficient of friction.

The pouches are disposable items designed for a single use.

BACKGROUND

The use of applicators for dispensing lotions, creams and ointments is well known. This mode of application has its origin in the pouring of liquids directly onto an absorbent material for immediate application. However, the inconvenience and waste associated with this practice led inevitably to the development of liquidproof packages containing pads impregnated with the desired liquid. One example of such a package is the lotion-applying pad described by Kudisch in U.S. Pat. No. 3,657,760.

The Kudisch-package consists of lotion-impregnated cotton batting enclosed in a liquidproof envelope. However, no membrane is provided for dispensing purposes and, instead, Kudisch brings the batting into direct contact with the skin. This type of application is not only unsanitary but it deposits on the skin a fibrous residue which can add to the patient's discomfort.

Moreover, Kudisch seals his package with a crimp roller and it is well-recognized in this field that such means cannot be relied upon to securely retain a liquid supply.

In U.S. Pat. No. 4,357,935 Frantzich describes an applicator package in which a medicinally impregnated gauze is hermetically sealed between two polyethylene layers. However, the gauze is not impregnated with liquid and there is no membrane to serve as a dispensing surface for topical application.

THE INVENTION

It is a feature of this invention to provide a composite or multi-layered pouch in which an absorbent pad is impregnated with the liquid which is to be dispensed. The layers are coextensive and they are joined peripherally by a heat seal.

A liquid-impermeable support layer directs the liquid through an overlying membrane while simultaneously providing the user with a protective backing.

A cover layer impervious to moisture and ambient air seals the package and protects the pouch contents from contamination and evaporation. The cover or top layer, like the support layer, is heat sealable and its high tensile strength allows it to be used as a peel-away covering.

One object of this invention is to provide a composite-type pouch in which the several layers, that is, the absorbent pad, the dispensing membrane, the support and the cover, extend laterally to an equal extent and share a common peripheral boundary.

Another object is to provide a pouch in which the absorbent layer has a discontinuous surface which is structurally contoured to provide enhanced liquid-storing capabilities.

A further object is to provide a pouch in which the absorbent layer is secured to the support via a lamina in the seal area.

Still another object is to provide a manufacturing method which is so economical that the pouch of this invention may be discarded after a single use.

These objects are achieved as the result of unique structural features in the composite layers:

(1) The absorbent layer is characterized by a discontinuous upper surface consisting essentially of a centrally disposed flat portion circumscribed by a continuous sidewall. This sidewall is peripherally bounded by a circumjacent attenuated border which extends laterally from the base of the sidewall to the peripheral edge or boundary. This layer is impregnated with the liquid which is to be dispensed.

(2) An impermeable support layer which is bonded to the flat lower surface of the absorbent layer;

(3) A dispensing membrane layer which intimately covers the upper surface of the absorbent layer. This membrane extends laterally to the peripheral edge of the pouch and forms a marginal border which is sealingly joined to the attenuated border of the absorbent layer; and (4) An impermeable cover layer which is removably secured to the marginal border of the membrane layer so that it can be separated for dispensing purposes.

A principal feature of this invention is the coterminous nature of its several layers among which the support layer, absorbent layer and dispensing membrane layer are joined by a non-rupturable heat seal, whereas, the cover layer is joined to the facing surface of the permeable membrane by a rupturable heat seal.

Another feature of this invention provides a finger-hold or starting point from which the cover layer can be separated and peeled away from the membrane surface. In this embodiment the facing edges of the cover layer and the dispensing layer are unsealed along their terminal edges so that an unsecured edge will protrude and allow the cover to be peeled off with relative ease.

The absorbent layer may be any natural or synthetic material which is flexible, compressible and capable of retaining large quantities of fluids. Typical of such materials are, for example, cotton batting and non-woven polyolefins such as melt blown polypropylene or polyester sponge and the like.

The impermeable support layer and the impermeable cover layer are derived from thermoplastic films which are impervious to moisture and ambient air. These include, for example, polyolefin films such as polyethylene and polypropylene. The polyolefin films are ideally suited for pouch construction because in addition to their impervious properties they form highly durable coverings which may be relied upon to withstand the wear associated with the handling and the transporting of packaged goods.

The permeable membrane may be any microporous film capable of transmitting fluids; however, the membrane must also possess the cohesive strength necessary to withstand the peeling effect which occurs when the cover layer is separated and removed. Any natural or synthetic film may be employed but long fiber porous paper is particularly suitable.

To ensure that the cover layer can be removed without rupturing the seal which joins the membrane to the underlying support layer the latter should be of larger guage than the former. In addition, the cover layer should be provided with a peelable heat seal, that is, the cover layer should exhibit a heat sealability factor which is lower than the sealability factor of the support web. In general, the peelable seal should fail at peel levels of about 1-2 pounds per inch, whereas, the seal which joins the membrane to the underlying support should fail at levels of 4-5 pounds per inch.

Typical of the liquids which may be dispensed in accordance with this invention are, for example, medicinal and cosmetic preparations such as hand creams, suntan lotions, nail polish remover, dermatological ointments, insect repellents and the like. Also, included are non-personal items such as furniture polish and abrasive cleansers and the like.

These and other objects of the invention are best understood by reference to the Drawings.

THE DRAWINGS

FIG. 1 is a top plan view of the pouch with the top layer partially removed.

FIG. 2 is a sectional view of the pouch shown in FIG. 1 along lines 2—2.

FIG. 3 is a sectional view of the pouch shown in FIG. 1 along lines 3—3.

FIG. 4 is a sectional view of the pouch of this invention shown in a dispensing mode with the cover layer removed.

FIGS. 5-13 illustrate a stepwise method for the manufacture of a liquid-containing pouch according to this invention.

FIG. 5 shows an array of shaped heat seal dies positioned above the composite of a support web and an absorbent pad layer.

FIG. 6 shows the sealing of the absorbent pad layer to the support web within the seal die areas.

FIG. 7 shows the step of impregnating the absorbent pad layer with a liquid.

FIG. 8 shows a permeable web which is in position for sealing to the impregnated absorbent pad layer in the seal die areas.

FIG. 9 shows the sealing of the permeable web layer to the impregnated absorbent pad layer.

FIG. 10 shows an array of shaped dies above a cover layer and in position for sealing onto the permeable web layer.

FIG. 11 shows the sealing of the cover layer to the permeable web layer.

FIG. 12 shows cutting means for separating the liquid-containing series of packages into individual units.

FIG. 13 shows the fingerhold which is formed on the liquid-containing packages as a result of the cutting operation.

This invention will now be illustrated by describing specific embodiments.

THE EMBODIMENTS

Figure 1:
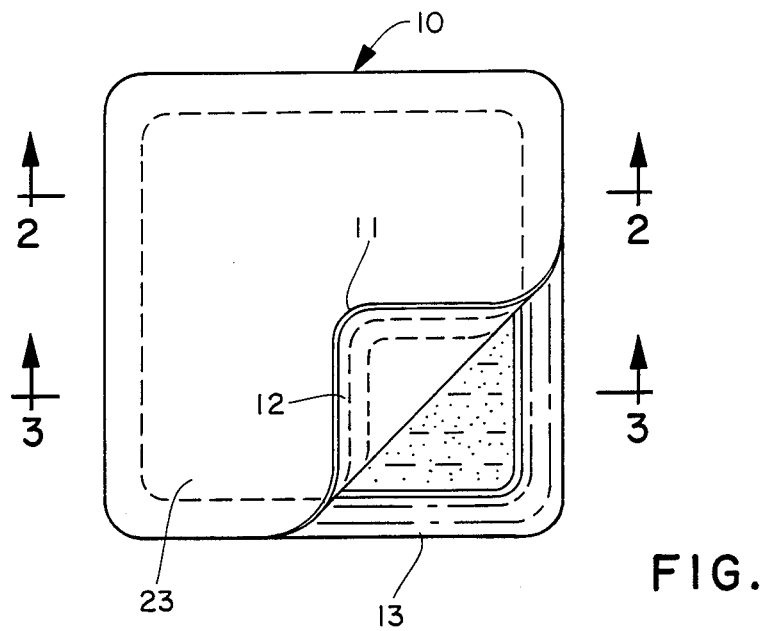
FIGS. 1-4 illustrate the structure of the liquid-containing pouch of this invention.

In FIG. 1 the pouch shown generally as 10 has an essentially square configuration with rounded corners; however, this is for illustration only and it is to be understood that the package may be of any desired size or shape.

Figure 2:
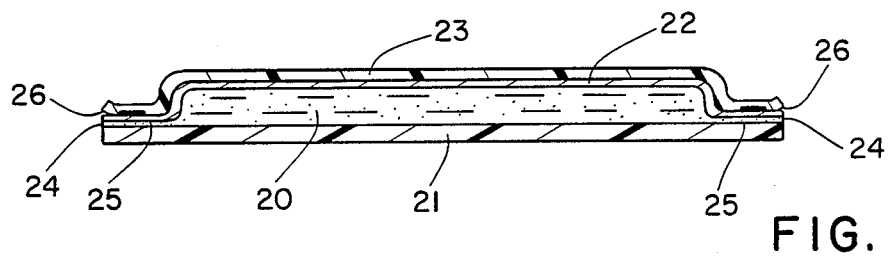
Figure 3:
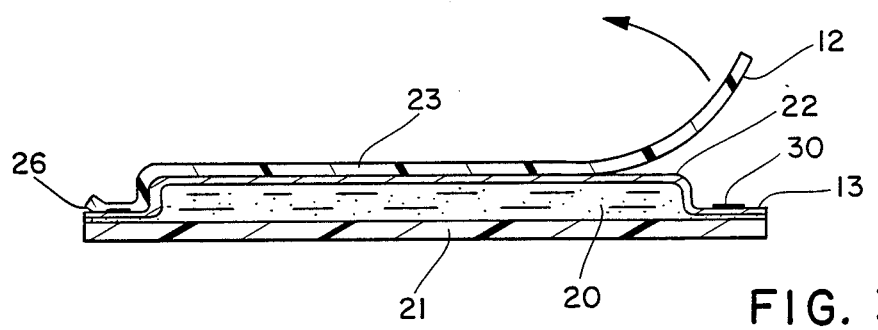

FIGS. 2 and 3 illustrate the composite structure of the pouch and the coterminus nature of its several layers. The liquid impregnated absorbent layer 20 is disposed on a support 21 which is both capable of withstanding the effects of handling and shipping while maintaining the seal by which it is joined to the lamina portion 25 of the absorbent pad.

A permeable membrane 22 covers the upper surface of the impregnated absorbent pad 20 to provide a dispensing surface. The membrane may be any microporous film which is pervious to fluids but it must also be capable of forming a rupturable seal on one surface and a non-rupturable seal on its opposite surface.

A cover layer 23 is superimposed on the membrane to provide a liquidproof package. This layer is also impervious to liquids and it may be derived from films identical to those which form the support layer 21; however, this cover layer must also form a rupturable seal with the membrane, that is, a seal which can be broken to peel away the cover without affecting either the dispensing surface or the seal which joins the opposite side of the membrane to its underlying support. Films capable of performing these dual functions include, for example, polyolefin films such as polyethylene and polypropylene.

The cover layer 23 is removed from the membrane 22 by taking hold of an unsecured corner 11 and lifting upwards and rearwardly as shown in FIG. 1. To ensure that a corner or some portion of the cover will always be available as a starting point the facing edge 12 of said cover and the facing edge 13 of said membrane are left unsealed to form the fingerhold identified as 26 in FIGS. 2 and 3.

Figure 4:
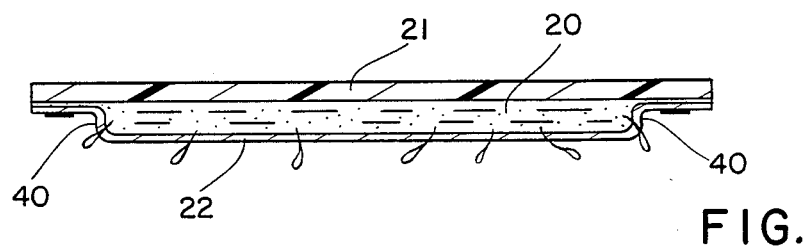

After the cover layer has been removed the liquid is dispensed as shown in FIG. 4. A lubricating quantity of fluid is brought to the surface of the membrane by squeezing the pouch prior to application and, thereafter, squeezing as needed. As a result, the dispensing surface becomes uniformly saturated and a thorough and smooth application is ensured.

A unique feature of this invention is the ability of the absorbent pad to hold large quantities of liquid in measured amounts. This is achieved by extending the absorbent pad laterally to its peripheral limits while simultaneously providing a centrally disposed depository in which relatively large amounts of the liquid may be held until needed.

This depository is that raised portion of the impregnated absorbent pad 20 which is bounded by the inner surfaces of membrane 22, support layer 21 and the continuous sidewall identified as 40 in FIG. 4. An attenuated segment or lamina portion 25 of the pad extends laterally between the membrane 22 and support layer 21 and terminates in the peripheral edge shown as 24 in FIG. 2. This segment or lamina 25 is the result of a sealing step which occurs in the process hereinafter described and it constitutes a barrier through which the liquid cannot escape.

This invention will now be illustrated by reference to the method by which the pouches are produced.

The pouch is prepared by the following sequence of steps:

(1) An absorbent pad containing thermoplastic material is joined to a support web by adhesive means or the application of heat seal dies. As a result of this operation the pad is joined to the support in the seal areas and a discontinuous surface is formed;

(2) The absorbent pad of the preceding step is impregnated with liquid following which a membrane or porous web is sealingly joined to the surface of the impregnated pad by the application of adhesive or heat seal dies in the seal areas;

(3) An impermeable sheet of thermoplastic film is secured to the membrane-covered pad of step (2) by the application of adhesive or shaped heat seal dies so as to provide a peelable cover; and (4) The serially produced pouches of step (3) are severed in the seal area to afford individual pouch packages.

Figure 5:
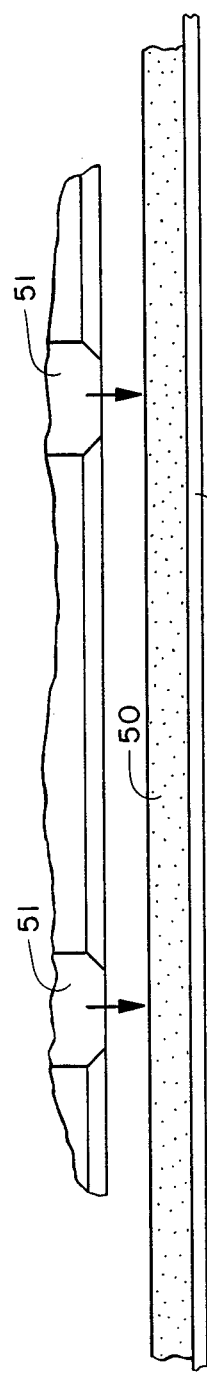

Referring now to the Drawings, a continuous absorbent pad 50 is unwound from a roll (Not shown) and it is passed onto a thermoplastic support web 21 beneath the heat sealing dies 51 (FIG. 5).

Figure 6:
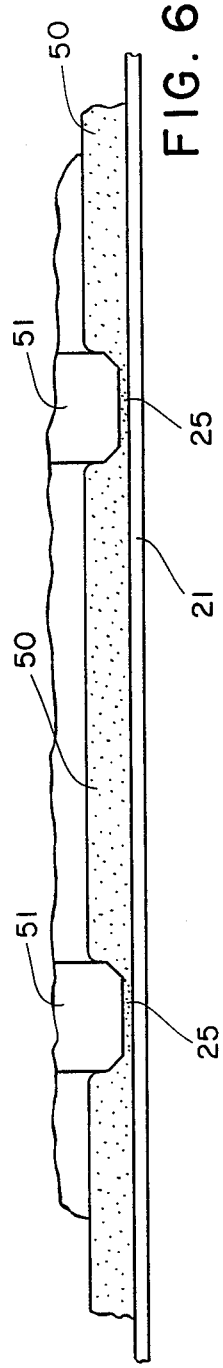
Figure 7:
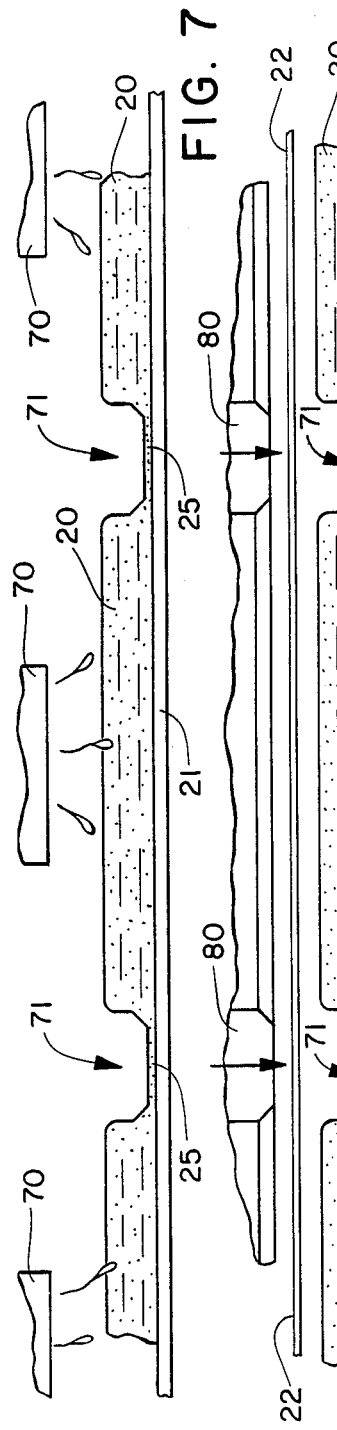

In FIG. 6 the dies 51 are shown in their sealing mode fully impressed into the pad 50. The heat imparted by the dies and the pressure which they exert are such that the absorbent layer becomes deformed in the seal areas and the support web melts slightly and penetrates into the absorbent layer to form the attenuated segment or lamina shown as 25 in FIG. 6. In this sealing step it is desirable to use a thermoplastic support web of relatively large guage because the added dimension enhances the fusing of the absorbent pad 50 to the support layer 21 and avoids any visible distortion of the backing. The seal formed by this step is non-rupturable to the extent that it can withstand peel levels of about 5 pounds per inch.

The impregnating of the absorbent pad 50 with a liquid is accomplished by distributing onto its surface from an overhead dispenser 70 controlled quantities of the desired fluid. The impregnation step may reach saturation levels but the attenuated segment or lamina 25 is so modified by the deformation and heat sealing step of FIG. 6 that it retains none of its original absorbent capabilities and it becomes instead a fluid barrier which effectively bars any liquid flow.

Figure 8:
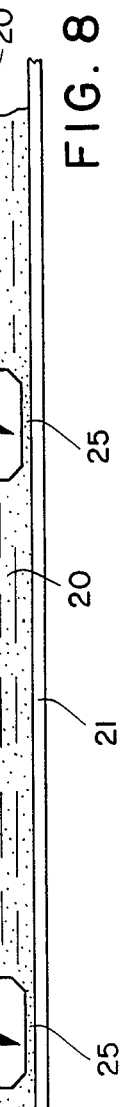

The introduction of a permeable membrane is achieved by passing a web of porous sheet material over the surface of the impregnated absorbent layer 20 as shown in FIG. 8. The heat seal dies 80 are then impressed onto the sheet material or membrane 22 in the seal areas 71 so as to bring said membrane into a sealing engagement with the lamina 25 (FIG. 9). The heat and pressure generated by this step results in the fusion of the membrane and lamina segments and the resulting seal is so secure as to be non-rupturable.

The cover layer is applied by passing a web of thermoplastic film 23 such as polyethylene or polypropylene over the discontinuous membrane layer 22 and applying a series of shaped heat seal dies 100 (FIG. 10).

When the shaped dies 100 are impressed onto the film or cover layer 23 the latter becomes fused to the membrane in the seal area 101. The dies 100 are characterized by a cutout portion 102 which limits their sealing engagement and affords the rupturable seals identified as 30 and 31 in FIG. 11. This seal fails at peel levels of less than 1-2 pounds per inch and it allows the cover layer 23 to be peeled away from the membrane 22 without exerting any adverse effect on the non-rupturable seals.

That web portion which lies between the rupturable seals 30 and 31, that is, the segment beneath the die cutout 102 (FIG. 11) remains unsealed and forms the arcuate blister shown as 120 in FIG. 12. Upon severing this blister with a cutting blade 121 the serial packages are separated into the individual pouches designated generally as 10 in FIG. 13. As a result of this cutting step a segment of the cover layer 23 extends upwardly to form a fingerhold 26 which can be used to rupture the seal 30 and peel away the cover.

If desired, gamma radiation can also be directed onto the packages to sterilize both their contents and the pouch exterior.

What is claimed is:

1. A flexible liquid-dispensing pouch consisting essentially of the following coterminous layers joined peripherally:
   (1) an absorbent layer impregnated with the liquid which is to be dispensed, said layer having an upper surface and a lower surface with the upper surface consisting essentially of a centrally disposed flat portion circumscribed by a continuous sidewall and including a circumjacent attenuated border which extends laterally from the base of said sidewall to the peripheral edge;
   (2) an impermeable support layer bonded to the lower surface of the absorbent layer;
   (3) a membrane layer disposed on the upper surface of the absorbent layer and extending laterally to form a marginal border which is sealingly joined to the attenuated border of the absorbent layer; and
   (4) an impermeable cover layer removably secured to the marginal border of the membrane layer for dispensing purposes.

2. The pouch of claim 1 wherein the facing surfaces of said cover layer and said dispensing layer are joined by a peelable heat seal.

3. The pouch of claim 1 wherein the facing surfaces of said cover layer and said dispensing layer include a terminal segment which is allowed to remain unsealed so that it may serve as a fingerhold for separating one layer from the other.

4. The pouch of claim 1 wherein the impermeable support layer is a polyolefin substrate.

5. The pouch of claim 4 wherein the substrate is selected from among polyethylene and polypropylene.

6. The pouch of claim 1 wherein the membrane layer is comprised of long fiber porous paper.

7. The pouch of claim 1 wherein the liquid is a medicinal or cosmetic preparation.

8. The pouch of claim 1 wherein the liquid is a polish or detergent.

9. The pouch of claim 1 wherein the liquid is an insect repellent.

* * * * *